United States Patent [19]
Gonzalez et al.

[11] Patent Number: 5,508,199
[45] Date of Patent: Apr. 16, 1996

[54] P450DB1 CLONES FOR IDENTIFYING HUMANS WITH GENETIC DEFECT IN DRUG METABOLISM

[75] Inventors: Frank J. Gonzalez, Bethesda, Md.; James P. Hardwick, Argonne, Ill.; Harry V. Gelboin, Chevy Chase, Md.; Urs A. Meyer, Basel, Switzerland

[73] Assignee: The United States of America as represented by the Department of Health and Human Services, Washington, D.C.

[21] Appl. No.: 242,158

[22] Filed: May 13, 1994

Related U.S. Application Data

[63] Continuation of Ser. No. 845,507, Feb. 27, 1992, abandoned, which is a continuation of Ser. No. 292,815, Jan. 3, 1989, abandoned.

[51] Int. Cl.$^6$ ............................ C12N 15/63; C07H 21/02; C07H 21/04
[52] U.S. Cl. .................. 435/320.1; 536/23.2; 536/23.5; 536/24.31; 435/172.3; 935/9; 935/14; 935/23
[58] Field of Search ........................ 435/6, 172.3, 320.1; 436/501, 94; 536/23.2, 27, 23.5

[56] References Cited

U.S. PATENT DOCUMENTS 4,683,194  7/1987  Saiki et al. .................................. 435/6

OTHER PUBLICATIONS

Fischer, "The Genetic Polymorphism of Debrisoqune/Sparteine Metabolism–Clinical Aspects", Pharmac. Ther. vol. 46, 1990, pp. 377–394.
Gonzalez, et al., "cDNA–expressed Human Cytochrome P450s: A New Age of Molecular Toxicology and Human Risk Assessment", Mutation Research, 1990, pp. 1–15.
Gonzalez, et al., "Evolution of the P450 Gene Superfamily: Animal–Plant 'warfare', Molecular Drive and Human Genetic Differences in Drug Oxidation", Trends in Genetics, vol. 6, No. 6, 1990, pp. 182–186.
Kimura, et al., "The Human Debrisoquine 4–Hydrozylase (CYP2D) Locus: Sequence and Identification of the Polymorphic CYP2D6 Gene, a Related Gene, and a Pseudogene", Am. J. Hum. Genet., 1989, 45:889–904.
Matsunaga, et al., "Sequence Requirements for Cytochrome P–450IID1 Catalytic Activity", Jour. Bio. Chem., vol. 265, No. 28, Oct. 5, 1990, pp. 17197–17201.
Matsunaga, et al., "The CyP2D Gene Subfamily: Analysis of the Molecular Basis of the Debrisoquine 4–Hydroxylase Deficiency in DA Rats", Biochemistry, 1989, pp. 7349–7355.
Henry Gee, "Bad Medicine", Nature–The Times News Service, London Times, Feb. 5, 1988.
Harold Schmeck, Jr., "Gene Defect Pinpointed in Bad Reactions to Drugs", New York Times, Feb. 4, 1988.
Science Notebook, "Genetic Defect May Cause Lack of Response to Drugs", Washington Post, Feb. 5, 1988.
Gonzalez et al., *DNA*, "Debrisoquine 4–Hydroxylose . . .", vol. 6, No. 2, 1987, pp. 149–161.
Skoda et al., *PNAS*, "Two mutant alleles of the human . . .", vol. 85, pp. 5240–5243, Jul. 1988.
Gonzalez et al., *Nature*, "Characterization of the common . . .", vol. 331, 4 Feb. 1988.
Gonzalez et al., *Genomics*, "Human Debnsoquine . . ." vol. 2, pp. 174–179 (1988).
Evans et al., *J. Med. Genet.* 17:101–105 (1980).
Gut et al., *FEBS Lett.* 173:287–290 (Aug., 1984).
Larrey et al., *Biochemistry* 23:2787–2795 (1984).

(List continued on next page.)

*Primary Examiner*—Margaret Parr
*Assistant Examiner*—Carla Myers
*Attorney, Agent, or Firm*—Townsend and Townsend Khourie and Crew

[57] ABSTRACT

A cloned cDNA encoding debrisoquine 4-hydroxylase gene and a probe for identifying humans having a genetic defect in the metabolism of a certain class of drugs of which debrisoquine is a model, have been prepared. Testing of new drugs and of humans by a simple assay has also been described.

5 Claims, 12 Drawing Sheets

OTHER PUBLICATIONS

Eichelbaum, *Fed. Proc.* 43:2298–2302 (May 15, 1984).
Nebert et al., *Trends Pharmacol. Sci.* 6:160–164 (Apr., 1985).
Gonzalez et al., *J. Biol. Chem.* 260:7435–7441 (Jun. 25, 1985).
Distlerath et al., *J. Biol. Chem.* 260:9057–9067 (Jul. 25, 1985).
Gonzalez et al., *J. Biol. Chem.* 261:10667–10672 (Aug. 15, 1985).
Gut et al., *J. Biol. Chem.* 261:11734–11743 (Sep. 5, 1986).
Meyer et al., *Xenobiotica* 16:449–464 (1986).
Eichelbaum et al., *Br. J. Clin. Pharmacol.* 23:455–458 (1987).
Kronbach et al., *Anal. Biochem.* 162:24–32 (1987).
Nebert et al., *Ann. Rev. Biochem.* 56:945–993 (1987).

```
HUMAN db1 (wt allele):    ATGGGGCTAGAAGCACTGGTGCCCCTGGCCGTGATAGTGGCCATCTTCCTGCTCCTGGTG
(Variant a ) :            ............................................................
(Variant b ) :            ............................................................
(Variant b') :            ............................................................
                                                   30                                        60

GACCTGATGCACCGGCGCCAACGCTGGGCTGCACGCTACCCACCAGGCCCCCTGCCACTGCCCGGGCTGGGCAACCTGCTGCATGTGGAC
............................................................................................
                  90                                  120                                 150

TTCCAGAACACACCATATACTGTCTTCGACCAG/GT-----(intron 1)-----AG/TTGCGGCGCCTTCGGGGACGTGTTCAGCCTGC
............................................................................................
                  180                                 210

AGCTGGCCTGGGACGCCGGTGGTCGTGTGGTGAATGGGCTGGTGGGCGTGCCGTGGCGAGGCTGGTGACCCGTGACCCCACGGCGAGGACACCGCGACCGCC
............................................................................................
                  240                                 270                                 300

CGCCTGTGCCCATCACCCAGATCCTGGGTTCCAAG/GT-----(intron 2)------AG//GGGTGTTCCTGGCGC
............................................................................................
                  330                                 360

FIG. 4A-1.
```

```
                    390                       420                       450
GCTATGGGCCCGCGTGGGCGGAGCAGAGGGCGCTTCTCCGTGTCCACCTTGCGCAACTTGGGCCTGGGCAAGAAGTCGCTGGAGCAGTGGG
                              C 480                                       510
TGACCGAGGAGGCCGCCTGCCTTTGTGCCGCCTTCGCCAACCACTCCG/GT-----(intron 3)------AG/GACGCCCCTTTCGCC
                                              G    AG                                   -

540                       570                       600
CCAACGGTCTCTTGGACAAAGCCGTGAGCAACGTGATCGCCTCCCCTCACCTGCGGGGCGCCGCTTCGAGTACGACGACCCCTCGCTTCCTCA 630                       660
GGCTGCTGGACCTAGCTCAGG-AGGGACTGAAGGAGGAGTCGGGCTTTCTGCGCGAG/GT-----(intron 4)-----AG/GTGCTGA
                  G    TC                            C 690                       720                       750
ATGCTGTCCCCGTCCTCCTGCATATCCCAGCGCTGGCAAGGTCCTACGCTTCCAAAAGCTTTCCTGACCCAGCTGGATGAGCTGC
                C    C
```

*FIG. 4A-2.*

```
                                                                    /GTGAGAGTG
          780              810                    840
TAACTGAGCACAGGATGACCTGGGACCCAGCCCCCCGAGACCTGAGGCCTTCCTGGCAGAGATGGAGAAG/GT---------
                                                                      /GT---------
                                      A              A   A            /GT---------
                                                     A   A
---(intron 5 normally spliced out)----------------------------
GCTGCCAGGTGGGGGGCAAGGGTGGTGGGTTGAGCGTCCCAGGAGGAATGAGGGAGGCTGGGCAAAAGGTTGGACCAGTGCATCACCCG
---(intron 5 normally spliced out)--------------------------
---(intron 5 normally spliced out)--------------------------

-AG/
GCGAGCCGCATCTGGGCTGACAGGTGCAGAATTGGAGGTCATTTGGGGGTCTACCCCGTTCTCTGTCCCGAGTATGCTCTCGGCCCTGCTCAG
                                                                              -AG/
                                                                              -AG/
                            870                 900               930
GCCAAGGGGAACCCTGAGAGCAGCTTCAATGATGAGAACCTGCGCATAGTGTGGCTGACCTGTTCTCTGCCGGGATGGTGACCACCTCG
                                              C  A                          T
                                                                       /GT---------
          G                                   G
          G                                   G
                              960
ACCACGCTGGCCTGGGCCCTCCTGCTCATGATCCTACATCCGGATGTGCAGC/GT---------
                                                    /GT---------
          C  T                            /GTGAGCCCAGCTGGGCCCAAGGCAGGGACTGAGGGA
-----(3' HALF OF EXON 6 LOST DURING REMOVAL OF INTRON 6)-----
```

*FIG. 4A-3.*

```
-----(intron 6 normally spliced out)-----------------------------------------------
-----(intron 6 normally spliced out)-----------------------------------------------
GGAAGGGTACAGCTGGGGGCCCCTGGGCTTAGCTGGGACACCCGGGGCTTCCAGCACACAGGCCGTGGCCAGGCTCCTGTAAGCCTAACTTCC
                                            990
                                                         -----AG/-GCCGTGTCCAACAGGAGATCG
                                                         -----AG/
                                                      ---AG/T
TCCAACACAGAGGAGGAAGGAGAGTGTCCCCTGGGTGCTGACCCATTGTGGGACGCATGTCTGTCCAG/T
                                                      ---AG/T
            1020                          1050                         1080
ACGACGTGATAGGGCAGGTGCGGGCGACCAGAGATGGGTGACCAGGCTCACATGCCCTACACCACTGCCGCCGTGATTCATGAGGTGCAGCGCT
                                                                                           A
                                                                                           A
            1110                          1140                         1170
TTGGGGACATCGTCCCCCTGGGTATGACCCATATGACATCCCGTGACATCGAAGTACAGGGCTTCCGCATCCCTAAG/GT-----
              G
              G
              G
                     1200                            1230
(intron 7) -----AG/GGAACGACACTCATCACCAACCTGTGCTCATCGGTGCTGAAGGATGAGGCCCGTCTGGGAGAAGCCCTACCCCGAA
```

FIG. 4A-4.

```
                    1260                                         1290
CACTTCCTGGATGCCCAGGGCCACTTTGTGAAGCCGGAGGCCTTCCTGCCTTTCTCAGCAG-------

1320                               1350                             1380
(intron 8)---AG/GCCGCCGTGCATGCCCTCGGGGAGCCCCTGGCCCGCATGGAGCTCTTCCTCTCTTCTTCACCTCCCCTGCTGCAGCAC 1410                            1440                                1470
TTCAGCTTCTCGGTGCCCACTGGACAGCCCCGGCCCCAGCCACCATGGTGTCTTT-GCTTCCTGGTGAGCCCATCCCCCTATGAGCTTTGT
                                                                                       C
                                              TC C      G CA     -   C
                                              TC C      G CA     -   C 1500                                1530                                   1560
GCTGTGCCCCGCTAGAATGGGGTACCTAGTCCCCAGCCTGCTCCTAGCCCCAGAGGCTCTAATGTACAAATAAAGCAATGTGGGTAGTTCC
                                                                        T
                                                                        T
(A)n
```

P450DB1 CLONES FOR IDENTIFYING HUMANS WITH GENETIC DEFECT IN DRUG METABOLISM

This is a continuation of application Ser. No. 07/845,507, filed Feb. 27, 1992, now abandoned, which is a continuation of Ser. No. 07/292,815, filed Jan. 3, 199 , now abandoned.

The present invention is related to a simple test for identifying humans having a genetic defect in the metabolism of a certain class of drugs of which debrisoquine is a model.

BACKGROUND OF THE INVENTION

Debrisoquine 4-hydroxylase is the only enzyme capable of metabolizing and inactivating drugs of which debrisoquine is a typical member. Debrisoquine is an adrenergic neuron blocking agent used in a number of countries to control blood pressure in hypertensive patients. In population studies of individuals given this drug, two distinct phenotypes have been described: the extensive metabolizers (EM) excrete 10 to 200 times more of the urinary metabolite 4-hydroxydebrisoquine than poor metabolizers (PM). In family studies the PM phenotype has been shown to behave as an autosomal recessive trait with an incidence between 5% and 10% in the white population of Europe and North America. The PM phenotype extends to the deficient metabolism of more than 20 commonly prescribed drugs (Idle et al, 1979, *Drug Metab. Rev.* 9, 301–317; Price-Evans, D. A. in *Ethnic Differences in Reactions to Drugs and Xenobiotics*, eds. Kalow et al, 491–526 Alan R. Liss, N.Y., 1986), including β-adrenergic receptor blocking agents, antiarrhythmics, antidepressants, the hallucinogen 4-methoxyamphetamine, and commonly used drugs such as the antitussive opioid dextromethorphan. Clinical studies have shown that PM individuals are at high risk with regard to the development of adverse side effects from these and many other drugs (Davies et al, 1981, *Br. J. Clin. Pharmacol.* 11, 88–91; Meyer et al, 1986, *Xenobiotica.* 16, 449–464). However, a genetic basis for this drug oxidation defect was heretofore not demonstrated.

SUMMARY OF THE INVENTION

It is, therefore, an object of the present invention to provide a simple test for identifying individuals with genetic defect in the metabolism of debrisoquine type of drugs.

It is another object of the present invention to provide cDNA clone of a gene directing the synthesis of a specific form of cytochrome enzyme designated P-450db1.

It is a further object of the present invention to provide cDNA clones of the mutant forms of the P450db1 gene, which produce incorrectly spliced db1 pre-mRNA.

It is yet another object of the present invention to provide debrisoquine 4-hydroxylase gene probe.

It is a still further object of the present invention to provide a diagnostic kit for identifying poor metabolizers (PM) of debrisoquine type drugs.

Other objects and advantages will become apparent from the following detailed description of the invention.

DESCRIPTION OF THE DRAWINGS

These and other objects, features and many of the attendant advantages of the invention will be better understood upon a reading of the following detailed description when considered in connection with the accompanying drawings wherein:

FIG. 1 shows the immunochemical correlation of anti-(rat)P450db1 with human liver bufuralol 1'-hydroxylase activity. (A) Inhibition of the microsomal hydroxyylase activity by the antibody against rat db1. Increasing amounts of antibody (IgG) or preimmune IgG were incubated with human liver microsomes at 4° C. for 30 min prior to assaying for bufuralol 1'-hydroxylase activity. The 100% of original hydroxylase activity represents 0.43 nmol/min/mg microsomal protein from an EM individual. (B) Inhibition of the purified db1 enzyme activity by anti-(rat)db 1. Human db1 was purified as described herein, infra. Preincubation of the antibody or preimmune serum was carried out as mentioned in (A) above. The 100% of original hydroxylase activity represents 12.9 nmol of product formed/min/nmol P450 in the reconstituted assay. (C) Western immunoblot analysis of 29 human liver microsomal samples with anti-(rat)db1. Electrophoretic separation of microsomal proteins (50 μg), electrotransfer to nitrocellulose filters, and immunoblot analysis with anti-(rat)db1 (20 μg IgG/ml) were carried out as described herein infra. (D) Histogram of bufuralol 1'-hydroxylase activity in 29 human liver microsomal samples. The eight individuals supplying specimens 12 through 29 were first phenotyped in vivo by quantitation of the urinary metabolites of either sparteine or debrisoquine before the microsomal activity was determined. The other samples were supplied by organ transport donors and assayed only in vitro; this protocol has been approved in advance by the hospital ethics committee. (E) Correlation of the immunochemically detectable protein with enzyme activity. The intensity of the Western immunoblot db1 bands (FIG. 1C) was quantitated with a CAMAG TLC Scanner in the reflection mode, and the results were compared with the respective bufuralol 1'-hydroxylase activities of 27 individuals by means of the Spearman rank-correlation [two samples were not included because of poor resolution on the Western immunoblots].

FIG. 3 shows the Northern hybridization analysis of RNA from the livers of four EM and three PM individuals. Each patient was first phenotyped by the bufuralol 1'-hydroxylase assay of liver microsomes in vitro (bottom), and another portion of each tissue was used for isolating poly(A)-enriched RNA. These 7 patients are included among the 29 individuals examined in FIG. 1. Each RNA sample (0.1 μg) was electrophoresed on 1% agarose-2.2M formaldehyde gels and transferred to Nytran filters. The filters were hybridized with a $^{32}P$-labeled nick-translated phP450db1 and (human) actin probes under suitable conditions. Autoradiography was carried out for 24 h at −80° C. with the aid of a Dupont Lightning-Plus intensifying screen. The three PM samples represent lanes 2, 5 and 7 and correspond to livers 20, 22 and 24 in FIG. 1B. Arrows a, b, b' and c represent the four mRNA variants that have been partially sequenced following cDNA cloning. RNA standards (Bethesda Research Laboratories, Inc.) were included and identified by hybridization of the filters with nick-translated DNA.

FIG. 4a shows the nucleotide sequence of the human wild-type (wt) db1 cDNA and of the cDNAs for variants a, b and b'. The intron-exon junctions were assigned on the basis of the partial sequencing of a human P450db1 genomic clone. The 5' portions of the variant cDNAs not sequenced are denoted by dots. The wt sequence 1s numbered; the variant sequences are shown only at those positions where there is no correlation. The initiation codon, possible base(s) involved in aberrant splicing, codon for cysteine that participates in the heme-binding site, termination codon, and the putative poly(A) addition signal are enclosed in blackened boxes.

FIG. 4b shows the diagram of the P450db1 exons and approximate sizes of the eight introns of the db1 gene. The normal splicing pattern of the wt pre-mRNA, and aberrant splicing patterns of the pre-mRNA from variants a, b and b' are illustrated. In order to explain the size of the b' mRNA (FIG. 3), the initiation of transcription most likely occurs from a cryptic promoter within intron 3. The normal db1 protein (497 amino acids) differs from the prematurely terminated, truncated proteins of all three variants. This probably results in unstable proteins that are so rapidly degraded that the anti(rat)db1 cannot detect these defective gene products.

FIG. 6 shows the segregation of polymorphic Xba I fragments in six families of PM propositi. Numbers indicate size of Xba I hybridizing fragments in kb. The individuals within a pedigree are placed above the corresponding lane. Arrows identify the proband; □ and ○, male and female subjects, respectively, with EM phenotype; ◪ and ◕, EM phenotype, obligate heterozygote by pedigree analysis; ■ and ◉ male and female subjects with PM phenotype; ⊗, phenotype not tested.

DETAILED DESCRIPTION OF THE INVENTION

The above and various other objects and advantages of the present invention are achieved by a cDNA clone of a gene encoding the expression of debrisoquine 4-hydroxylase (db1) in mammalian cell culture.

Unless defined otherwise, all technical and scientific terms used herein have the same meaning as commonly understood by one of ordinary skill in the art to which this invention belongs. It is noted that any methods and materials known in the art which are similar or equivalent to those mentioned herein can be used in the practice or testing of the present invention. All publications mentioned hereunder are incorporated herein by reference. Unless mentioned otherwise, the techniques employed herein are standard methodologies well known to one of ordinary skill in the art and can be found described in such publications as Skoda et al, 1988, Proc. Natl. Acad. Sci. USA, 85:5240–5243; Gonzales et al, 1988, Nature, 331:442–446 and Gonzales et al, 1988, Genomics, 2:174–179, all of which are included herein in toto by reference. The cloned gene, the product thereof(db1), the anti-db1 antibodies and the bufuralol assay used standard procedures and such procedures per se are not a part of the S present invention.

FIG. 1 provides convincing evidence that the antibody against rat P450db1 recognizes the human enzyme involved in the debrisoquine polymorphism. For these studies, the β-adrenergic blocking agent bufuralol was used as the prototype substrate for the human P450db1 enzyme, because a highly sensitive assay for bufuralol 1'-hydroxylase activity has been developed (Kronback et al (1987) Anal. Biochem. 162, 24–32). Anti-(rat)P450db1 serum inhibits human liver microsomal bufuralol 1'-hydroxylase (FIG. 1A) and the human purified db1 in an in vitro reconstituted enzyme assay (FIG. 1B).

Figure 1A:
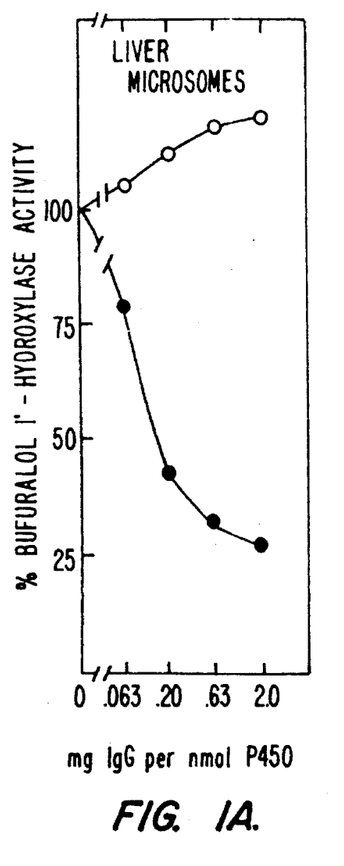
Figure 1B:
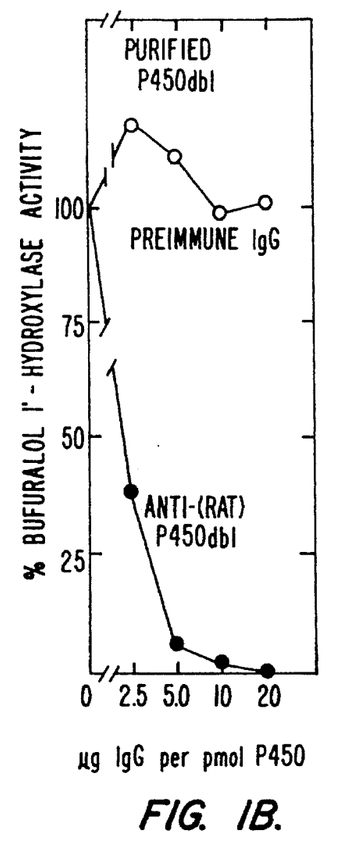
Figure 1C:
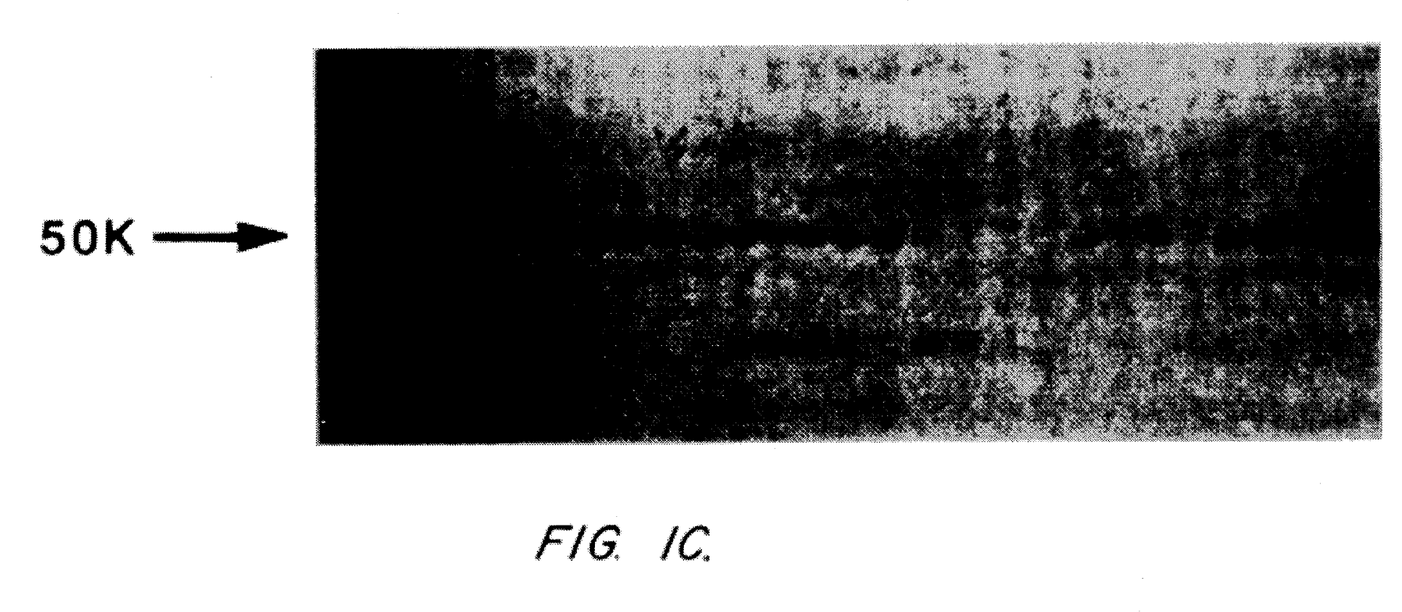
Figure 1D:
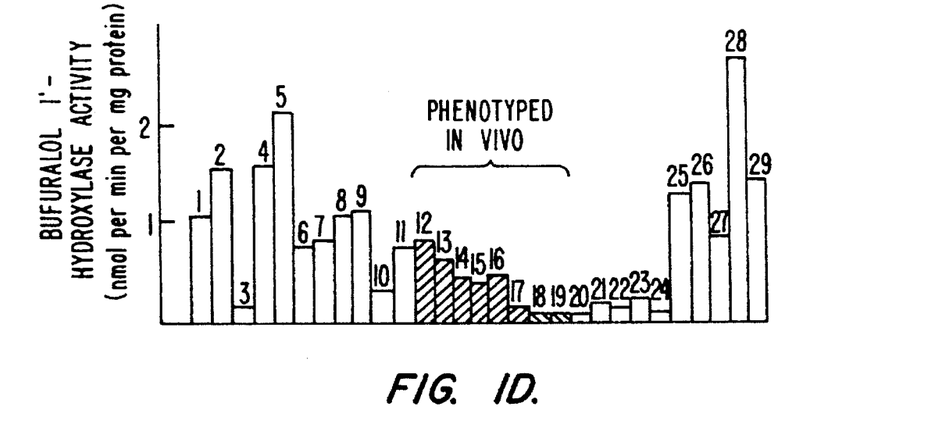
Figure 1E:
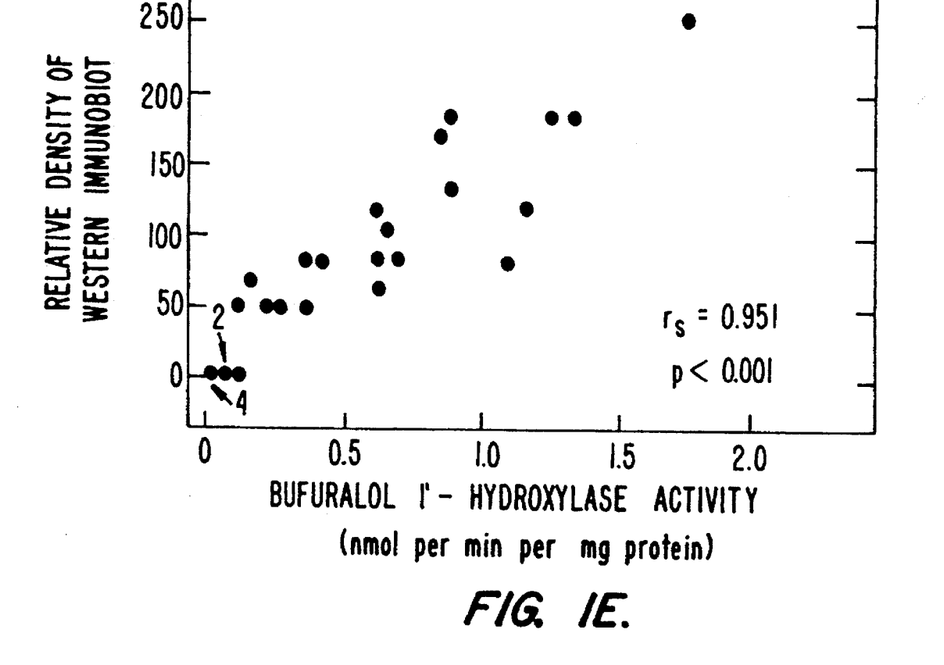

Using anti-(rat)db1, it was possible to quantitate on Western lmmunoblots the amount of human db1 protein in 29 liver samples (FIGS. 1C & 1D). The microsomal bufuralol 1'-hydroxylase activity (FIG. 1E) was highly correlated with the concentration of immunodetectable human db1 protein ($M_r$~50,000). Using the previously prepared antibodies against human P450 with high bufuralol or debrisoquine hydroxylase activities, no correlation was found between the immunoreactive protein and enzymic activity; presumably, other proteins of identical molecular weight are recognized by these antibodies. The results of FIG. 1 indicate that the antibody to rat P450db1 can be used to isolate the human db1 cDNA.

Using a human λgt11 expression library constructed from poly(A) mRNA from the liver of an EM individual, a 1568-base pair cDNA clone was isolated by screening with anti-(rat)db1. Analysis of the deduced amino acid sequence verified that this cDNA resides in a distinct subfamily within the P450II gene family (Nebert et al (1987) Annu. Rev. Blochem. 56, 945–993). The db1 cDNA probe was used to rescreen two other human cDNA libraries, each constructed from an EM liver. Several cDNAs were isolated, partially sequenced, and found to be identical to db1, suggesting that, in contrast to the rat, the only active hepatic P450 gene in the human IID subfamily is db1.

Figure 2:
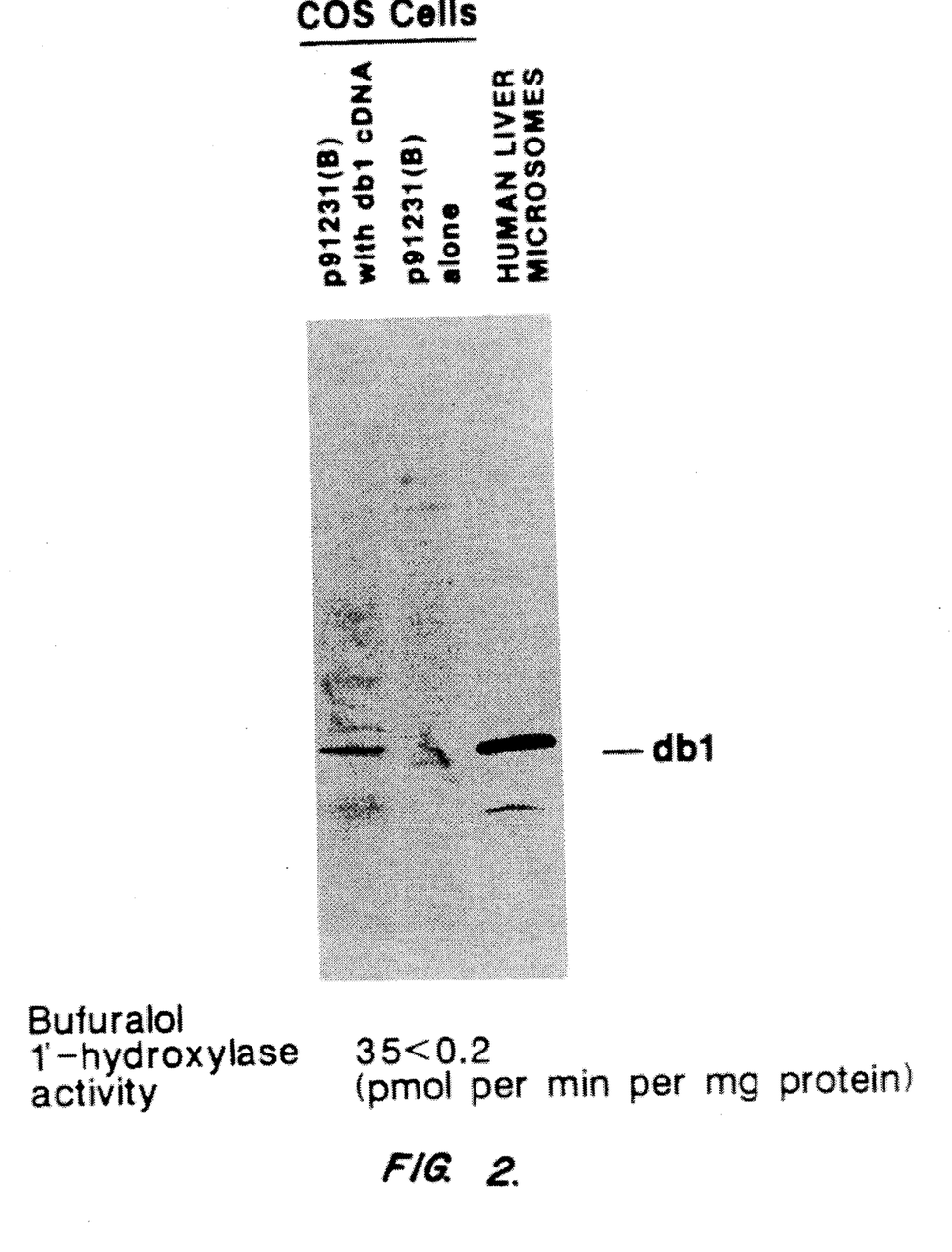
FIG. 2 shows the results of Western immunoblot analysis of monkey COS cells transfected with p90231(b) containing the human db1 cDNA or with the p91023(B) vector alone. The db1 cDNA included 12 bases upstream from the initiation codon to 44 bases downstream from the termination codon. The cells were grown in 175-cm$^2$ flasks until about 50% confluent, following which they were transfected with 25 μg of plasmid DNA. Cell extracts were prepared by sonication 72 h after transfection, and the protein (50 and 60 μg in lanes 1 and 2, respectively) was assayed by Western blot analysis using anti-rat db1 antibody and for bufuralol 1'-hydroxylase activity. Human microsomal protein (50 pg) from an EM liver was used as a positive control.

To demonstrate that the db1 cDNA codes for the appropriate P450 enzyme having bufuralol 1'-hydroxylase activity, the cDNA was inserted into the SV40- and adenovirus-based expression vector p91023(B) and the construct was transfected into COS cells. Western immunoblot analysis of total extract from transfected cells (FIG. 2) revealed a protein that comigrated with human liver microsomal db1 protein; these cells expressed high bufuralol 1'-hydroxylase activity. The db1 protein was absent in cells transfected with the vector alone, and these cells contained no detectable bufuralol 1'-hydroxylase activity. These results verify the identity of the db1 cDNA.

Figure 3:
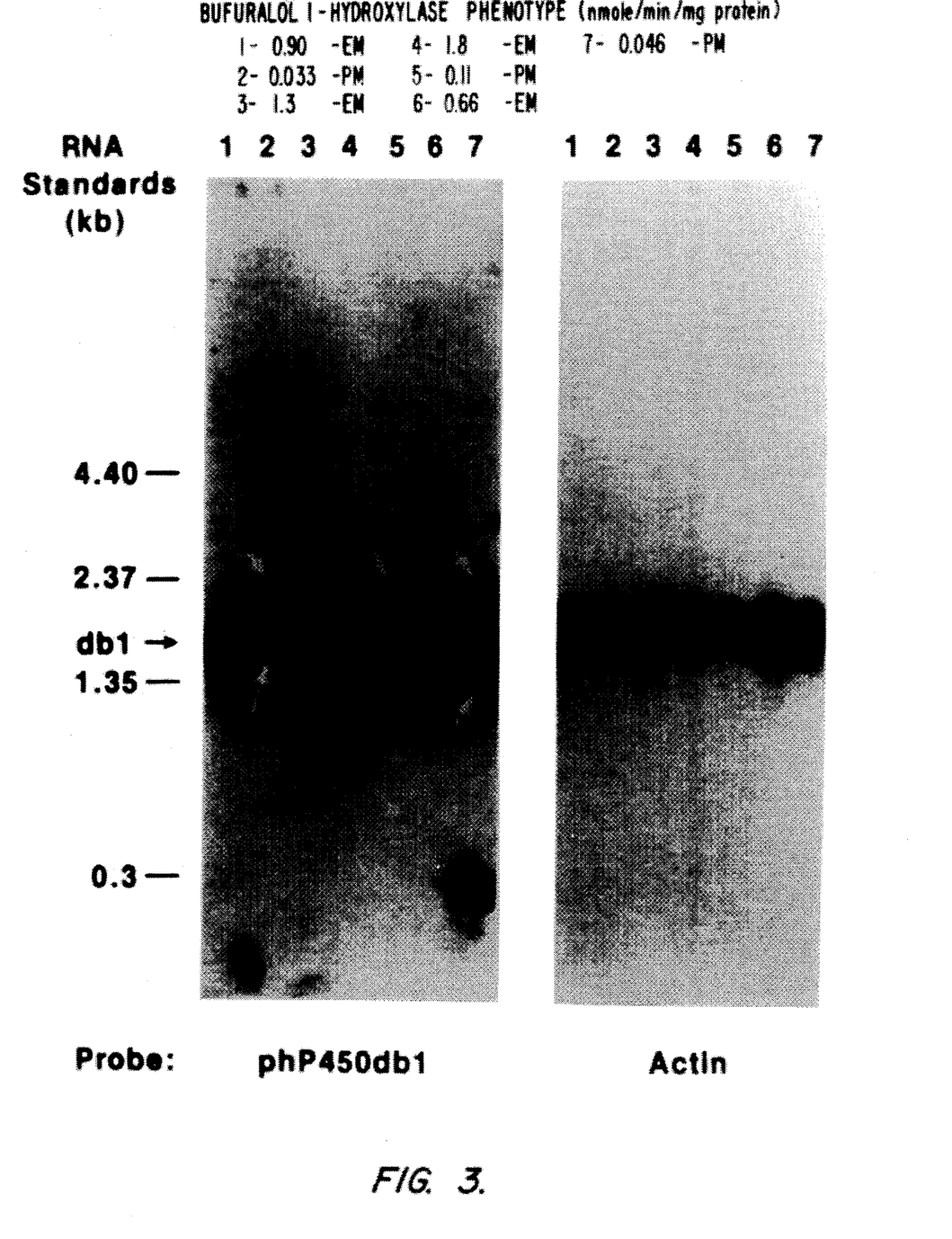

To study the molecular basis of the debrisoquine polymorphism, Northern blot analyses were performed on mRNA from seven livers studied in FIG. 1, including three PM livers with markedly decreased bufuralol 1'-hydroxylase activity (FIG. 3; lanes 2, 5 & 7). In all four EM livers exhibiting high bufuralol 1'-hydroxylase activity (FIG. 3; lanes 1, 3, 4 & 6), the probe hybridized to an mRNA of about 1.8 kb. Variant mRNAs a and b (arrowed) are larger than, variant mRNA b' is considerably smaller than, and variant mRNA a is of similar size to, the db1 wild-type (wt) mRNA. If the RNA detected with the db1 probe is normalized to the level of human actin mRNA, the quantity of the 2.1-kb variant a mRNA (lanes 2 & 5) is similar to that of the 2.1-kb variant b mRNA (lane 7). The small hybridization signal in the wt db1 mRNA region of lanes 5 and 7 is about 1000-fold less intense than the wt mRNA in EM livers and is probably due to cross-hybridization of the probe to other mRNAs in the P450II family. Increasing the filter hybridization or washing stringency totally abolishes these small hybridization signals. A probe derived from the 3' nontranslated region of the db1 mRNA also does not detect an mRNA in lanes 5 and 7 that is the same size as the normal wt db1 mRNA. The FIG. 3 data thus suggest that the PM samples in both lanes 2 and 7 possess at least two RNA species, while the PM sample in lane 5 possesses at least one RNA species, related to db1 mRNA.

To determine the nature of the mRNAs detected in the PM livers examined in FIG. 3, λgt11 eDNA libraries were constructed and then screened with the db1 eDNA probe. Two classes of db1 eDNA from liver 2, one class from liver 5, and two classes from liver 7 were isolated from the eDNA libraries. At least 15 cDNAs from each library were thus characterized.

Figure 4A:
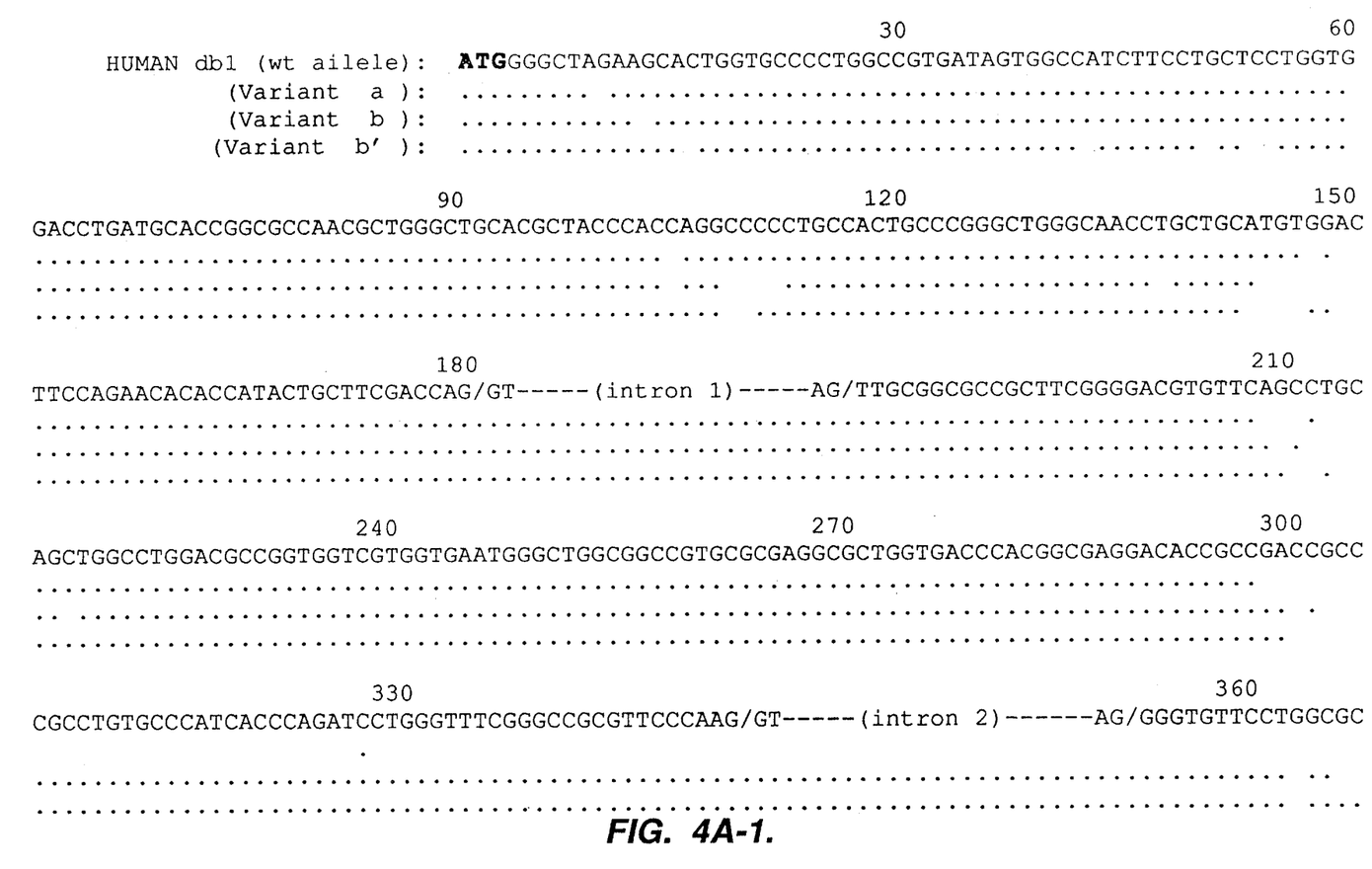
Figure 4A:
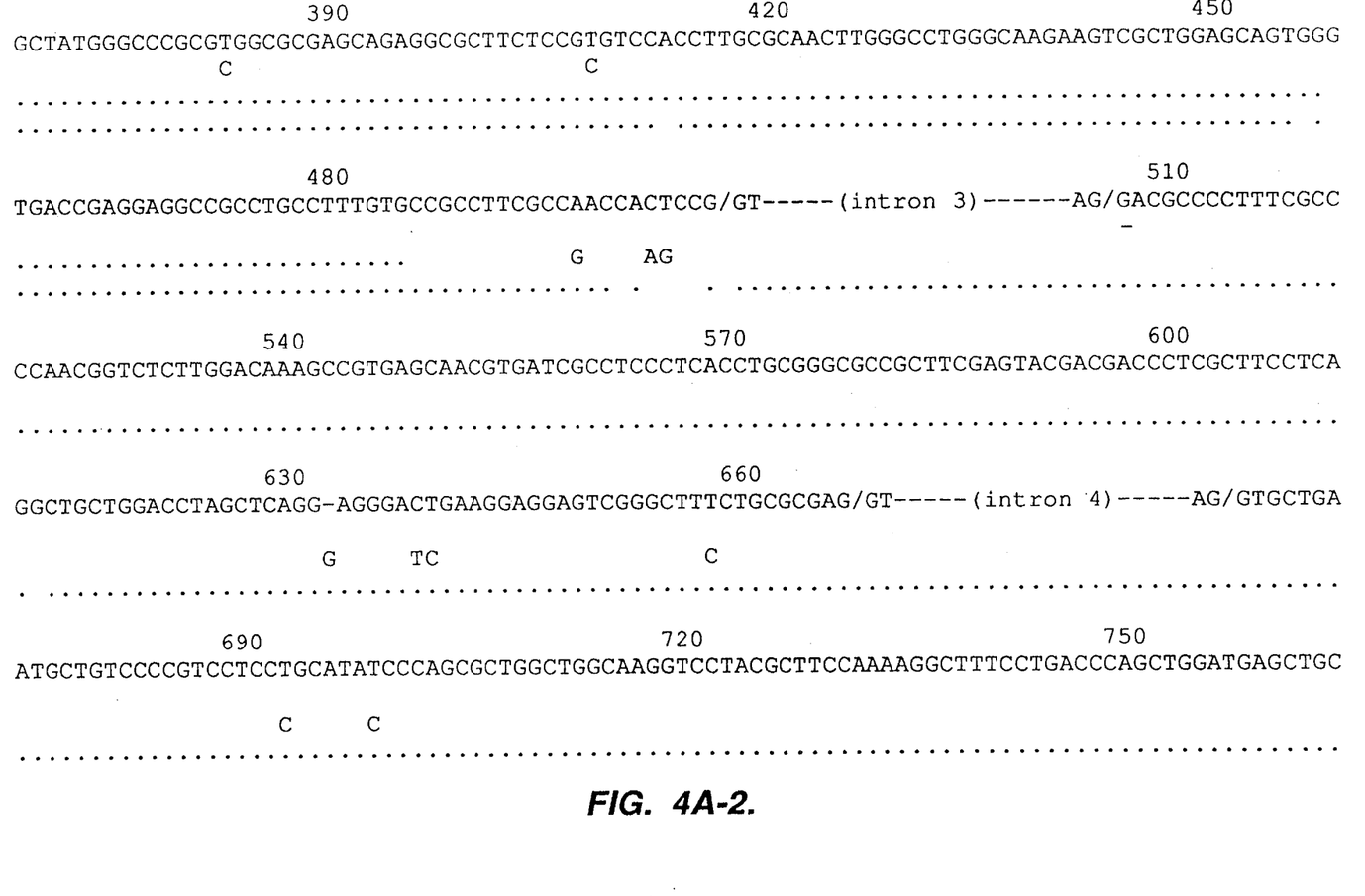
Figure 4A:
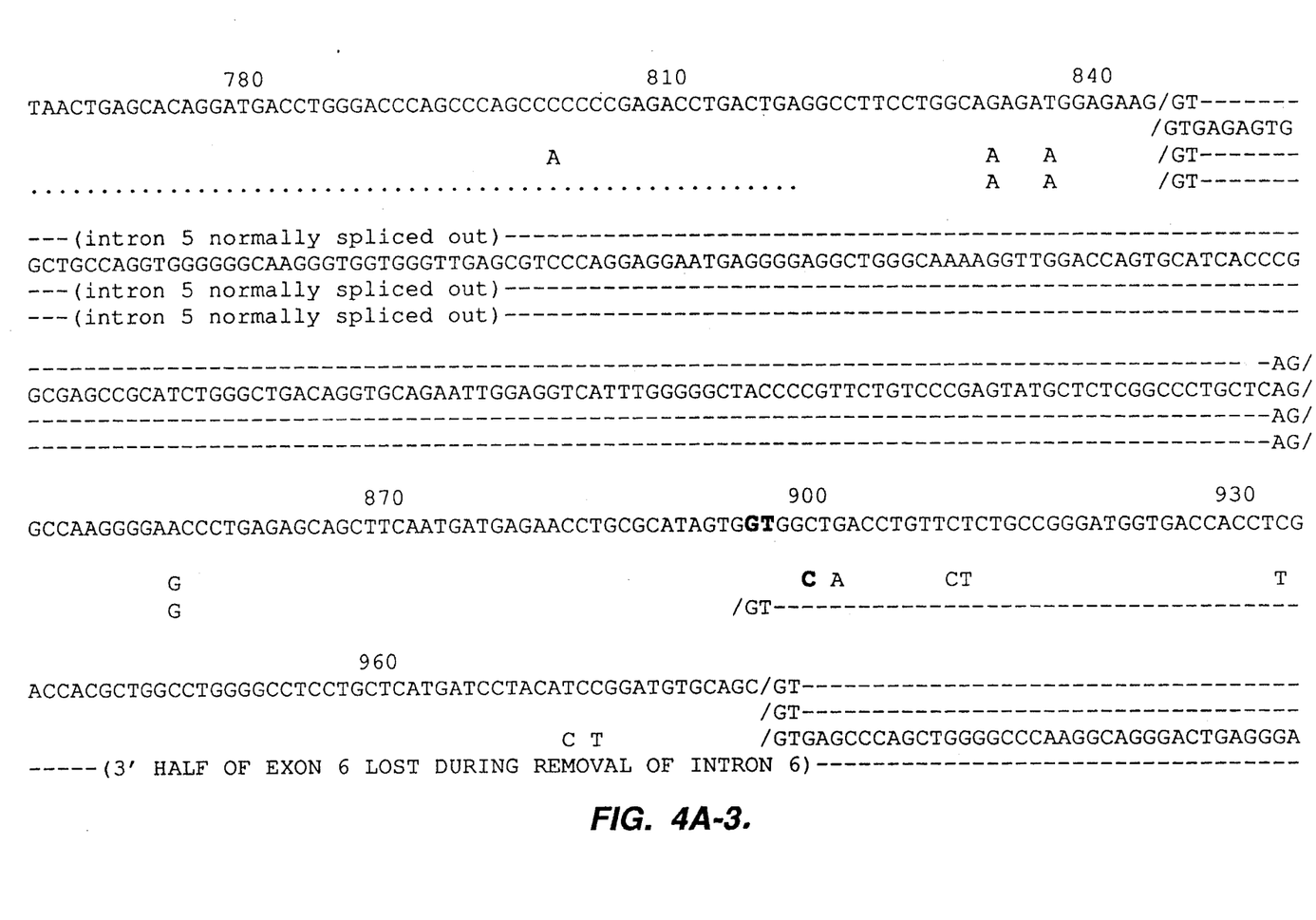
Figure 4A:
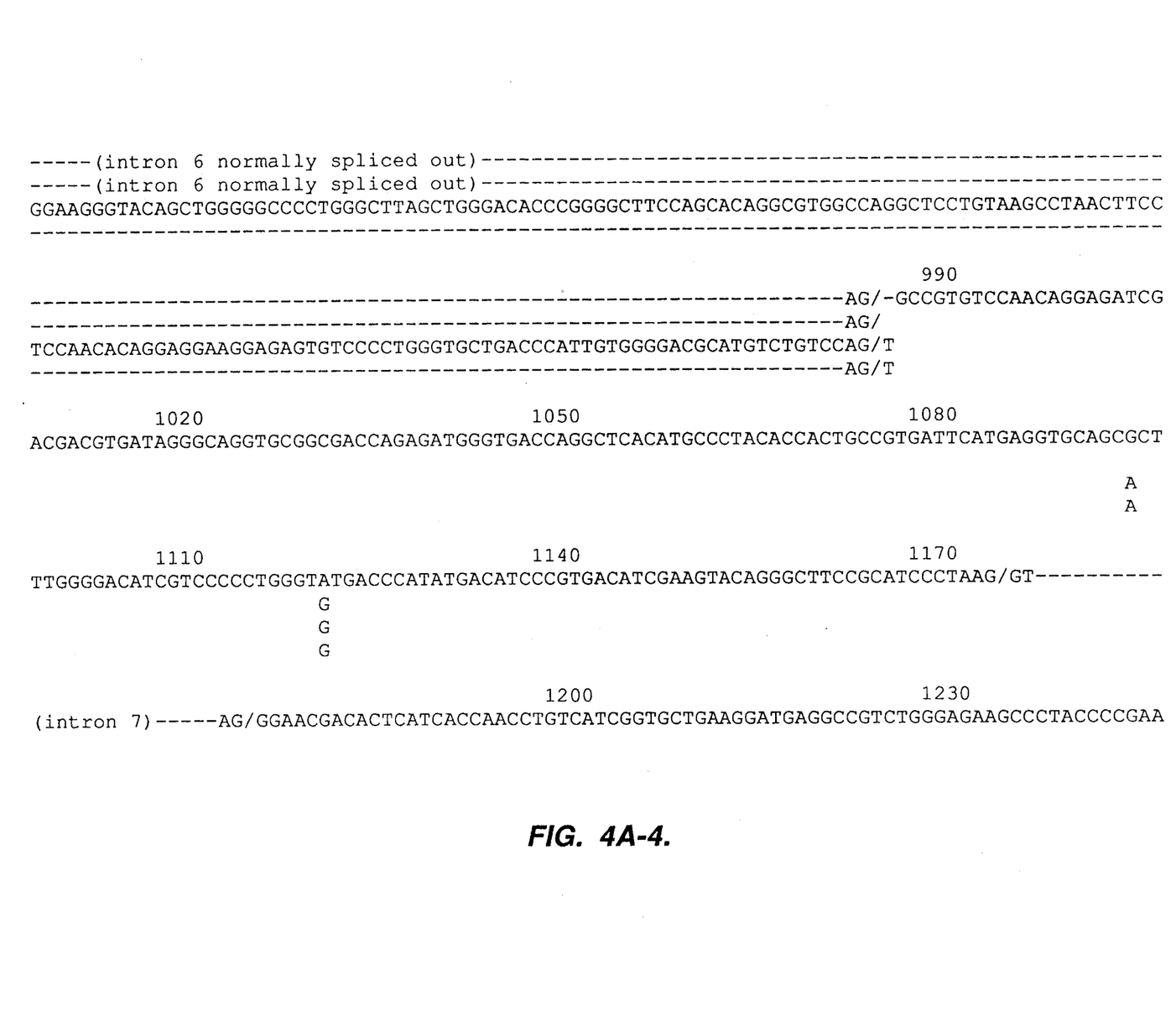
Figure 4A:
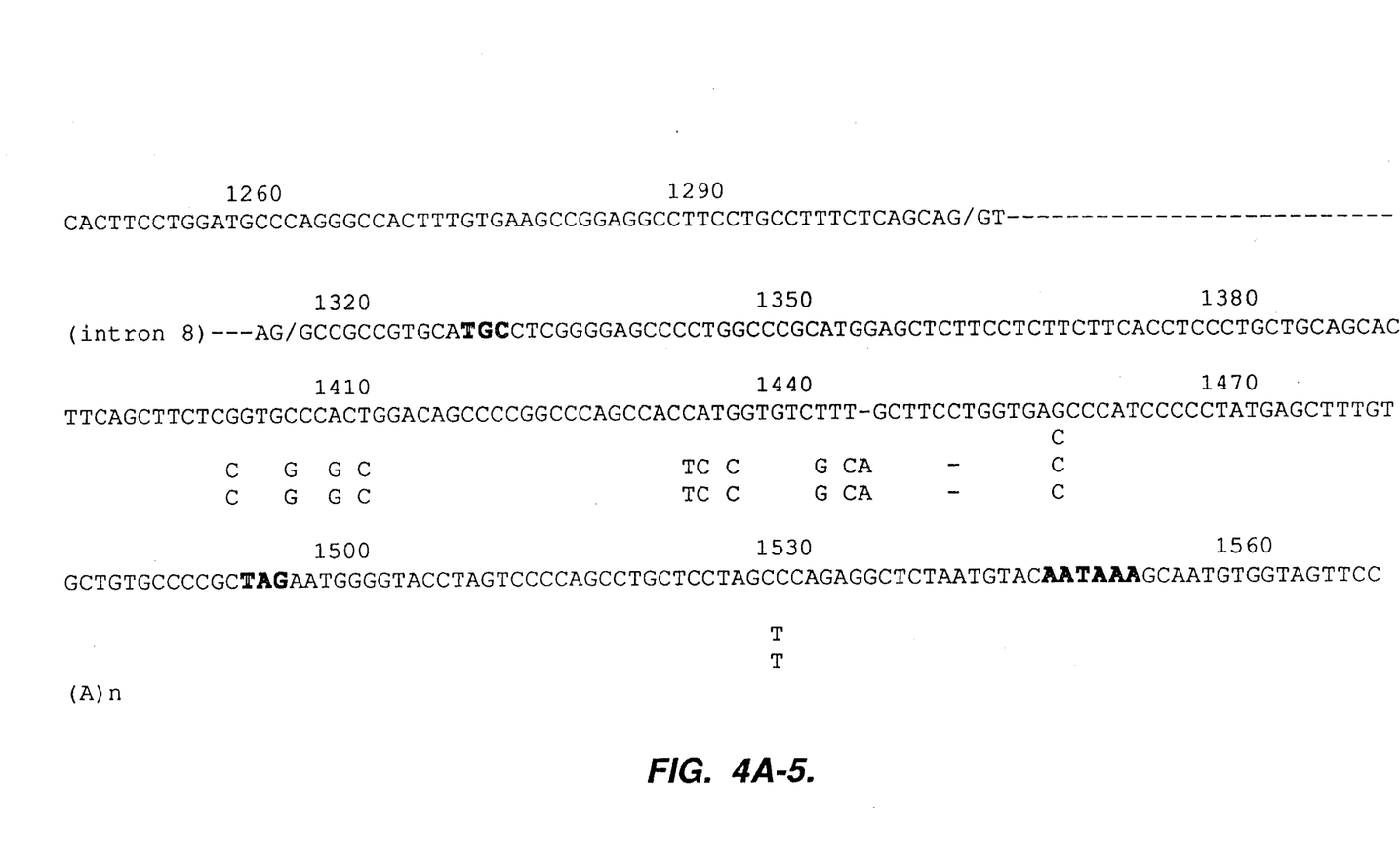
Figure 4B:
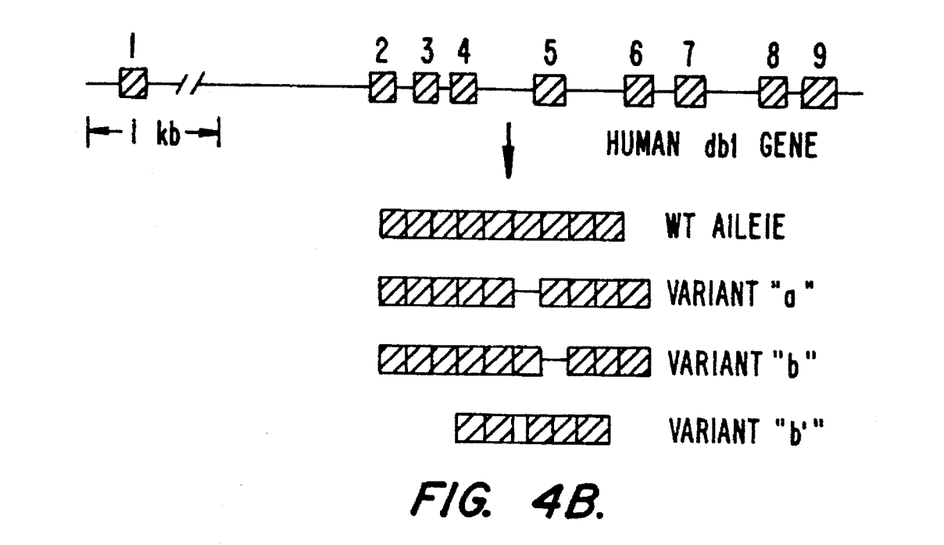

It was found that variant a from both livers 2 and 5 retained intron 5 (FIG. 4), variant b from liver 7 retained intron 6, and variant b' from liver 7 lost the 3' half of exon 6 in combination with the removal of intron 6. That these clones represent nuclear RNA precursors is unlikely, because at least four individual cDNA clones of each of the b and b' variants, three individual cDNA clones of variant a from the liver 5 library, and three individual cDNA clones of variant a from the liver 2 library were partially sequenced across their respective variant regions and found to be identical. Further, the fact that variant mRNAs a and b are larger and variant mRNA b' is smaller than the wt db1 mRNA (FIG. 3) is consistent with the aberrant splicing defects observed by sequencing (FIG. 4).

Sequencing of variant c cDNA from liver 2 revealed that the protein was identical to that of the wt db1 protein, except for several amino acid substitutions (data not presented). Liver 2 had a very low but detectable amount of db1 protein and very low bufuralol 1'-hydroxylase activity, but much of this residual activity could be inhibited by anti-(rat)db1, in contrast to the lack of inhibition of residual bufuralol 1'-hydroxylase activity in liver microsomal samples 5 and 7 (in which no db1 protein is detectable). These data suggest that liver 2 has one mutant allele that gives rise to variant a mRNA, from which a normal P450 protein is not produced, and another allele that produces a normal-sized mRNA that is presumably translated into a partially altered and/or unstable protein. However, this hypothesis remains to be verified.

Although full-length cDNAs for variants a and b were not obtained, it is postulated that both mRNAs contain the complete 5' end and thus are transcribed from the normal initiation start site. This conclusion is based on the lengths of the RNAs and the fact that these RNAs hybridize to a 300-bp probe (5'-most 300 bases) derived from the normal db1 mRNA. In contrast, variant b' mRNA is approximately 1.0 kb in length (FIG. 3) and does not hybridize with this 300-bp 5' db1 probe. It is, therefore, likely that the transcription of variant b' might be initiated from an artificial promoter region that formed after the original gene-inactivating base change had taken place. Because the variants b and b' cDNA sequences are identical in their common coding and 3' noncoding regions, it is likely that the retention of intron 6 in variant b and the aberrant splice (use of a cryptic promoter) in variant b' arise from the same mutation(s), whatever it might be. The possibility that both variant b and b' mRNAs are derived from the same allele cannot, therefore, be excluded at this point.

Of interest is the fact that both variant mRNAs a and b contain the normal GT/AG consensus exon-intron junction signal, suggesting that base change(s) in another less obvious spliceosome recognition region might cause the mutation in these db1 genes. In fact, if these mutant genes were directly sequenced, the observed defects (intron retention; partial exon removal; initiation from cryptic promoter) would not have been readily apparent. Sequencing of the entire normal human P450db1 gene (introns, exons and flanking regions) is necessary before the base mutations that cause the aberrant splicing defects in these mutant P450db1 genes can be fully understood. It is well known that abnormal mRNA often leads to an unstable protein product.

In summary, the data presented herein clearly establish that the basis of the "poor metabolism" phenotype is, in the majority of cases examined, an absence of detectable human liver microsomal P450db1 protein. How many other mutant alleles are responsible for the PM phenotype remains to be determined.

It is particularly noteworthy that the PM phenotype exhibits deficient metabolism not only toward debrisoquine and bufuralol but also toward a growing list of approximately two dozen drugs, such as desmethylimipramine, dextromethorphan, ecainide, guanoxan, nortriptyline, methoxyamphetamine, metoprolol, perhexiline, phenacetin, phenformin, propranolol, sparteine and the like. New drugs related to the debrisoquine polymorphism are being developed each year; identification of the PM individual prior to administering any of these drugs would thus be of great value to the practicing physician. Moreover, the successful expression of the db1 cDNA-encoded enzyme activity (FIG. 2) in COS cells, having no detectable P450-mediated drug metabolism background, would allow an assay in which new drugs being developed can be tested to see whether they fall into this particular drug oxidation polymorphism following the procedure similar to that described herein for debrisoquine.

Figure 5:
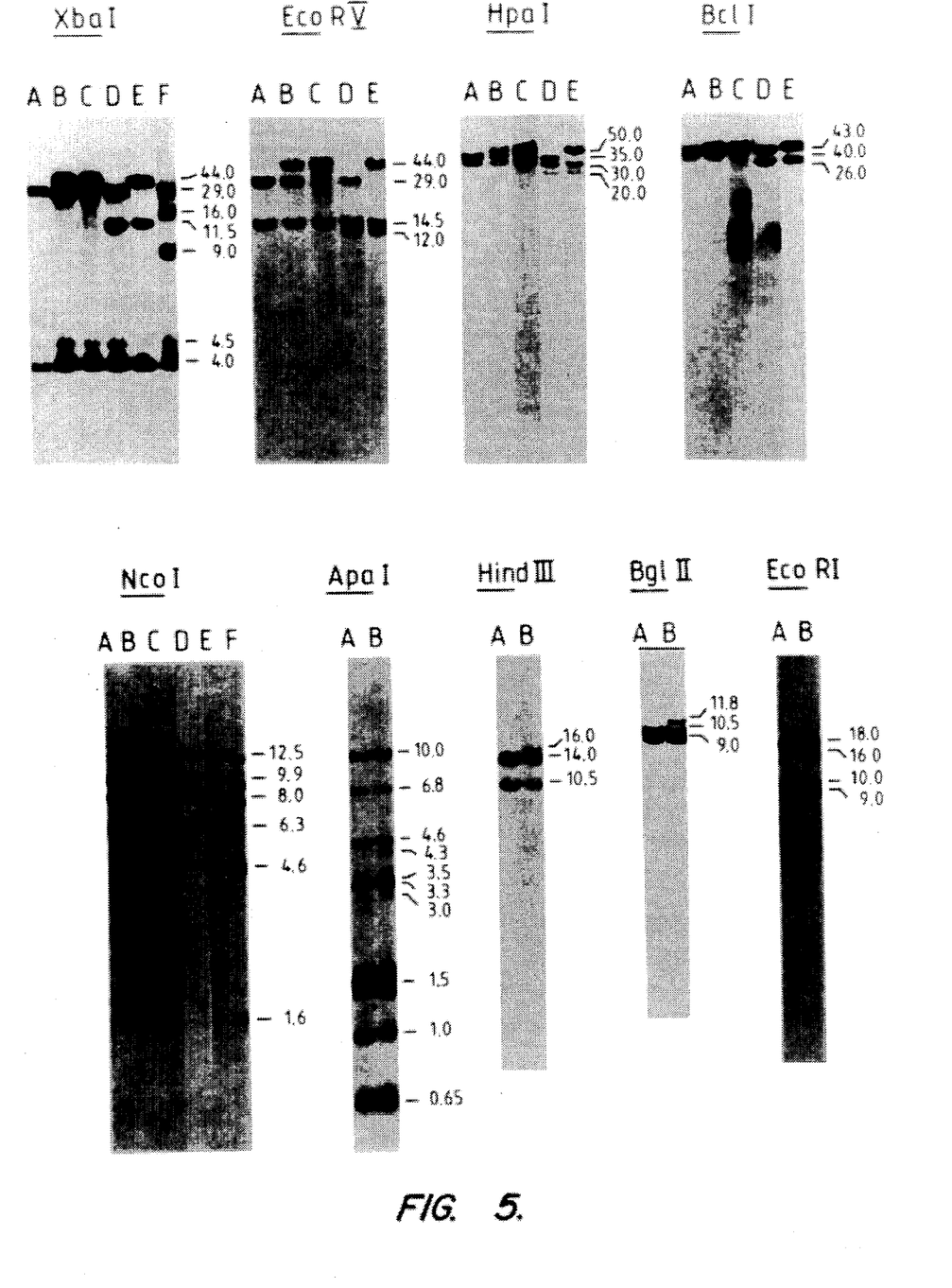
FIG. 5 shows Southern blot analysis of human leukocyte DNA after digestion with nine restriction endonucleases and hybridization with the $^{32}$p-labeled full-length P-450db1 cDNA probe. One example for each observed restriction pattern (53 individuals examined) is shown. Numbers indicate fragment size in kb.
Figure 6:
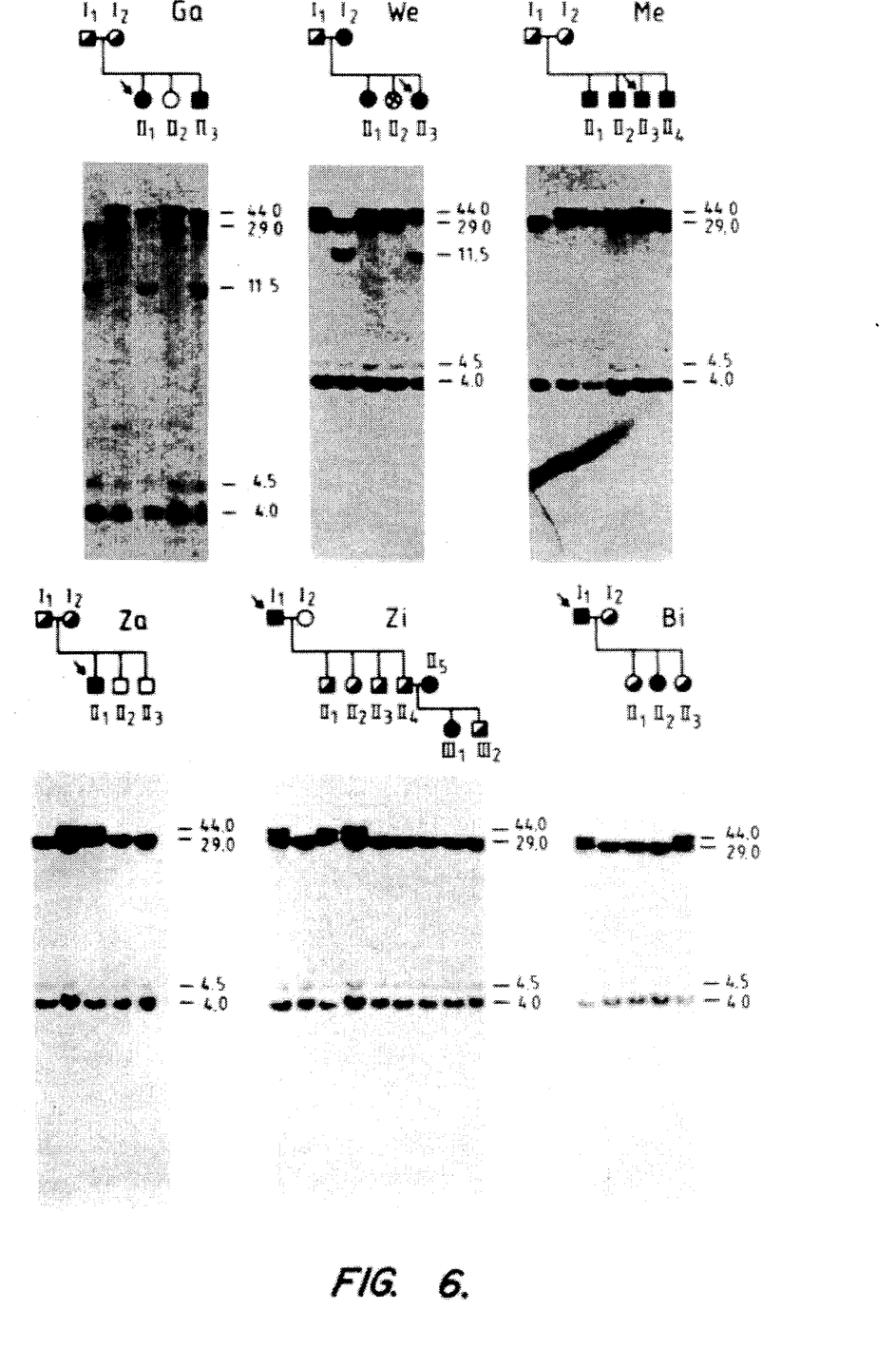

Results of restriction fragment length polymorphism (RFLP) study using various restriction enzymes are shown in Tables 1 and 2 (Skoda et al, supra) and FIGS. 5 and 6. The data clearly demonstrate clinical application of the present invention.

The study populations consisted of 53 healthy, unrelated Caucasian individuals: 29 EM (♀:20, ♂:9) and 24 PM (♀:15, ♂:9) were studied. In addition six PM families with a total of 29 family members were investigated.

Phenotyping Procedure. Clinical test data and blood from EM and PM subjects were collected according to protocols approved by the ethics review boards of the institutions providing samples. Most subjects were phenotyped with debrisoquine [10 mg oral administration (p.o.)], except for seven subjects with sparteine (100 mg p.o.) and six subjects with dextromethorphan (20 mg p.o.). It has been established that these three test drugs provide identical information on the phenotype (Dayer et al., *Biochem. Pharmacol.* 36:4145–4152 (1987), Schmid et al., *Clin. Pharmacol. Ther.* 38:618–623 (1985), and Evans et al., *J. Med. Genet.* 20:321–329 (1983). PM individuals were identified by a urinary metabolic ratio of >12.6 for debrisoquine/4-OH-debrisoquine (Dayer, supra), >20 for sparteine/2- and 5-dehydrosparteine (Dayer, and Evans, supra), and >0.3 for dextromethorphan/dextrorphan (Schmid, supra).

Nucleic Acid Procedures. Blood (30–50 ml) was obtained from each individual, and DNA was isolated from peripheral leukocytes as described (Nietzel, *Hum. Genet.* 73: 320–326 (1986). Human leukocyte DNA (5 µg) was digested to completion with restriction endonucleases, and Southern blotting (McBride et al., *Proc. Natl. Acad. Sci.* 83:130–134 (1986)) was done by using Biotrace RP membranes (Gelman) and hybridization probes prepared by nick-translations with [α-$^{32}$P]dCTP (3000 Ci/mmol, Amersham; 1 Ci=37 GBq) to a specific activity of 1–3×10$^8$ dpm/μg of DNA.

It is understood that the examples and embodiments described herein are for illustrative purposes only and that various modifications or changes in light thereof will be suggested to persons skilled in the art and are to be included within the spirit and purview of this application and scope of the appended claims.

TABLE 1

Analysis of Xba I RELPS in unrelated individuals of EM and PM phenotypes

| Xba I pattern (FIG. 1) | Polymorphic fragments, kb | EMs (n = 29) | | | PMs (n = 24) | | |
|---|---|---|---|---|---|---|---|
| | | n | Genotype† | Pattern frequency | n | Genotype† | Pattern frequency |
| A | 29 | 26 | D/D or D/d | 0.9 | 6 | d/d | 0.25 |
| B | 44/29 | 1 | d°/D | 0.03 | 9 | d°/d | 0.37 |
| C | 44 | — | — | — | 1 | d°/d° | 0.04 |
| D | 29/11.5 | — | — | — | 4 | d/d* | 0.17 |
| E | 44/11.5 | — | — | — | 4 | d°/d* | 0.17 |
| F | 29/16 + 9 | 2 | | 0.07 | — | — | — |

†D designates the normal 29-kb allele; d(29 kb), d°(44 kb), and d*(11.5 kb) designate mutant alleles. The expected genotypes for the EM phenotype are: D/D, D/d, D/d°, and D/d*; for the PM phenotype, they are: d/d, d/d°, d/d*, d°/d*, d°/d°, and d*/d*.

TABLE 2

Phenotypes and genotypes in families of 6 PM individuals

| | MR | Phenotype | Genotype |
|---|---|---|---|
| Family GA | | | |
| I$_1$ | Dx 0.1 | EM | D/d* |
| I$_2$ | Dx 0.1 | EM | D/d° |
| II$_1$ | Dx 9.7 | PM | d*/d° |
| II$_2$ | Dx 0.3 | EM | D/d° |
| II$_3$ | Dx 9.1 | PM | d*/d° |
| Family We | | | |
| I$_1$ | 3.4 | EM | D/d° |
| I$_2$ | Dx 2.2 | PM | d/d* |
| II$_1$ | 69.0 | PM | d°/d |
| II$_2$ | ND | ND | d°/d |
| II$_3$ | 56.3 | PM | d°/d* |
| Family Me | | | |
| I$_1$ | 1.0 | EM | D/d |
| I$_2$ | 0.5 | EM | D/d° |
| II$_1$ | 22.4 | PM | d/d° |
| II$_2$ | 41.8 | PM | d/d° |
| II$_3$ | 21.5 | PM | d/d° |
| II$_4$ | 68.8 | PM | d/d° |
| Family Za | | | |
| I$_1$ | 0.7 | EM | D/d |
| I$_2$ | 1.6 | EM | D/d° |
| II$_1$ | 23.4 | PM | d/d° |
| II$_2$ | 0.2 | EM | D/D or d/D |
| II$_3$ | 0.8 | EM | D/D or d/D |
| Family Zi | | | |
| I$_1$ | 34.3 | PM | d/d° |
| I$_2$ | 0.2 | EM | D/D or D/d |
| II$_1$ | 0.3 | EM | d°/D |
| II$_2$ | 0.2 | EM | d°/D |
| II$_3$ | 0.4 | EM | d/D |
| II$_4$ | 0.4 | EM | d/D |
| II$_5$ | 78.6 | PM | d/d |
| III$_1$ | 332.0 | PM | d/d |
| III$_2$ | 0.5 | EM | D/d |
| Family Bi | | | |
| I$_1$ | 45.0 | PM | d/d° |
| I$_2$ | 1.1 | EM | D/d |
| II$_1$ | 1.3 | EM | d/D |
| II$_2$ | 55.0 | PM | d/d |
| II$_3$ | 0.9 | EM | d°/D |

The phenotype was determined in urine collected after administration of debrisoquine except in six individuals, where dextrometorphan was used (data indicated by Dx). The number of the family member refers to the position in the pedigree given in FIG. 2. For explanation of genotype symbols, see the legend to Table 1. MR, metabolic ratio; ND, not determined.

What is claimed is:

1. An isolated and purified cDNA clone of a human P450db1 gene which encodes and expresses debrisoquine 4-hydroxylase in a mammalian cell comprising the wild-type sequence shown in FIG. 4a.

2. An isolated nucleotide sequence comprising a nucleotide sequence of human P450db1 as shown in FIG. 4a and encoding human debrisoquine 4-hydroxylase wherein the nucleotide sequence is selected from the group consisting of the wild-type sequence, the variant (a) sequence, the variant (b) sequence, and the variant (b') sequence.

3. The isolated nucleotide sequence of claim 2 which encodes wild-type human debrisoquine 4-hydroxylass.

4. A recombinant plasmid which comprises DNA having the sequence of claim 3.

5. A recombinant plasmid adapted for expression in a mammalian cell, which comprises the cDNA of claim 1 and operably linked regulatory elements necessary for expression of the cDNA in the mammalian cell.

* * * * *